US006183473B1

United States Patent
Ashman

(12) United States Patent
(10) Patent No.: US 6,183,473 B1
(45) Date of Patent: Feb. 6, 2001

(54) VARIABLE ANGLE CONNECTION ASSEMBLY FOR A SPINAL IMPLANT SYSTEM

(76) Inventor: Richard B Ashman, 1407 First St., New Orleans, LA (US) 70130

( * ) Notice: Under 35 U.S.C. 154(b), the term of this patent shall be extended for 0 days.

(21) Appl. No.: 09/296,104

(22) Filed: Apr. 21, 1999

(51) Int. Cl.$^7$ .................................................. A61B 17/56
(52) U.S. Cl. .............................................................. 606/61
(58) Field of Search ................................. 606/61, 62, 60, 606/72

(56) References Cited

U.S. PATENT DOCUMENTS

| | | | |
|---|---|---|---|
| 5,261,909 | * | 11/1993 | Sutterlin et al. ........................ 606/61 |
| 5,282,801 | * | 2/1994 | Sherman ................................. 606/61 |
| 5,611,800 | * | 3/1997 | Davis et al. ............................ 606/61 |
| 5,634,925 | * | 6/1997 | Urbanski ................................. 606/61 |
| 5,643,262 | * | 7/1997 | Metz-Stavenhagen et al. ....... 606/61 |
| 5,643,263 | * | 7/1997 | Simonson ............................... 606/61 |
| 5,688,272 | * | 11/1997 | Montague et al. ..................... 606/61 |
| 5,785,711 | * | 7/1998 | Errico et al. ............................ 606/61 |
| 5,976,135 | * | 11/1999 | Sherman et al. ....................... 606/61 |
| 5,980,521 | * | 11/1999 | Montague et al. ..................... 606/61 |
| 6,001,098 | * | 12/1999 | Metz-Stavenhagen et al. ....... 606/61 |

* cited by examiner

Primary Examiner—Michael Buiz
Assistant Examiner—Tan-Uyen Thi Ho

(57) ABSTRACT

A spinal implant assembly includes an elongated spinal implant, such as a rod, implanted adjacent the spine, and a bone fastener, such as a bone screw, engaged within a vertebra. A connection assembly includes a first member having a first opening for receiving the rod, and a second member having a second opening for receiving an elongated stem of the bone fastener. The two members are connected to permit relative rotation between the two members to accommodate variable angular orientations of the bone screw relative to the rod. A single washer is provided that has an opening for positioning over a portion of both the first member and the second member. One face of the washer is configured to engage the rod, while the opposite face of the washer is configured to engage the stem of the bone screw. In one embodiment, the opposite face of the washer defines a plurality of radial splines. The stem of the bone screw includes an interface element in the form of a rib that is configured to interdigitate with the radial splines. In another embodiment, the opposite face of the washer and the stem of the bone screw include interdigitating or interlocking raised features, such as knurling or cross-hatching. A set screw and threaded bore are provided in the first member, with the set screw bearing against the rod, which then bears against the washer and bone screw stem to clamp the assembly together.

14 Claims, 4 Drawing Sheets

VARIABLE ANGLE CONNECTION ASSEMBLY FOR A SPINAL IMPLANT SYSTEM

BACKGROUND OF THE INVENTION

The present invention relates generally to the field of spinal implant systems, and particularly systems that employ elongated spinal implants, such as rod and plates, connected at various locations along the spinal column. More particularly, the invention concerns a connection assembly that provides variable angle and variable height adjustability to the elongated spinal implant relative to a bone fastener engaged to the spine.

Several spinal fixation systems have been developed for use in correcting and stabilizing sections of the spinal column and facilitating spinal fusion. In one such system, a bendable elongated spinal implant, such as a rod, is longitudinally disposed adjacent the vertebral column and then secured to various vertebrae along the length of the column by way of a number of bone fasteners or fixation elements. A variety of bone fasteners can be utilized, such as hooks or bone screws, which are configured to engage specific portions of a vertebra.

An example of one such system is the TSRH® Spinal System of Sofamor Danek Group, Inc. In this system, various hooks and bone screws are engaged to a spinal rod by way of eyebolts. In early versions of the TSRH® Spinal System, the vertebral hooks and bone screws were attached to the spinal rod at a fixed orientation, usually projecting perpendicularly below the rod. At the time, the TSRH® Spinal System presented a significant advance over prior systems in its VERSATILITY, strength of fixation, and ease of implantation.

However, one drawback faced by the original TSRH® Spinal System, as well as the other prevalent fixation systems, was that a surgeon was required to make significant adjustments to the contour of the bendable rod so that the bone fasteners could solidly engage the vertebral bodies. What was needed, then, was a bone fastener that could be connected to the spinal rod at a variable angle. In order to address this need, the TSRH® Variable Angle Screw was developed, as described in U.S. Pat. No. 5,261,909. This Variable Angle Screw utilized the same TSRH® eyebolt to achieve a connection to a spinal rod. In addition, the Variable Angle system incorporated a washer that fit over the eyebolt, engaged the spinal rod within a groove in one surface of the washer, and provided a radially splined surface facing the bone fastener. The bone fastener had a complementary splined surface so that the fastener could be situated at variable angular orientations relative to the spinal rod. A nut threaded onto the post of the eyebolt clamped all the components together to complete the assembly.

The Variable Angle Screw system of the '909 Patent presented a significant advance over prior rod-based implant systems. The system of the '909 Patent was relatively compact and required a minimal number of parts yet was able to accomplish a solid fixation of the bone fastener to the rod at a wide range of angular orientations. One drawback of the system was that the eyebolt-nut combination required side-tightening of the nut to clamp the system together. This side-tightening aspect required a larger surgical site about the spine so that a wrench could be manipulated. To address this difficulty, a top-tightening assembly was developed as disclosed in U.S. Pat. No. 5,282,801. The clamp assembly depicted in the '801 Patent replaced the eyebolt and nut with a clamp body having a T-bar against which the head of the variable angle bone fastener was clamped. In addition, while the original TSRH® System relied upon tightening a nut against the variable angle bone screw, the top-tightening approach of the '801 Patent utilized a set screw that acted against the spinal rod to push the spinal rod into the interlocking washer, and ultimately against a complementary spline face of the variable angle screw. With this system, the variable angle capability was retained, while a top-tightening feature was added.

With the addition of the top-tightening capability, the more recent TSRH® Spinal System has provided surgeons with a great deal of flexibility in the placement and orientation of bone fasteners, such as hooks and screws, relative to a spinal rod. The Variable Angle components greatly reduce the need to manipulate and bend the spinal rod to conform to the patient's anatomy. Even with the great improvements presented by the TSRH® Spinal System, a certain amount of shaping or contouring of the spinal rod has still been required. Specifically, the rod must be shaped so that at the point of attachment of the bone fastener, the rod is the same distance from the vertebral body as the splined or interdigitating portion of the bone fastener. This vertical or height alignment is necessary so that the variable angle components are properly aligned for accurate connection when the assembly is clamped together. Thus, the spinal surgeon still has to spend a certain amount of time shaping the spinal rods during the surgery so that the fixation system can be properly implanted.

In order to address this difficulty, later systems were developed that provided for a certain degree of vertical adjustability. By vertical or height adjustability, it is meant adjustment along the length of the bone fastener. Adjustment in this dimension allows the rod to be situated at varying distances from the spine, or oriented with a pre-set contour regardless of the location of fastener.

An adaptation of the original variable angle screw concept of the '909 Patent is presented in U.S. Pat. No. 5,611,800. This system retained the yoke configuration of the bone screw in the '909 Patent, but added a multi-faceted connecting feature on both surfaces of the yoke. While the '800 Patent system added height adjustability it did so at the cost of a more complicated connector structure with four specially machined interdigitating surfaces.

Another approach has been suggested in U.S. Pat. No. 5,643,263. The connection assembly in the '263 Patent uses a Schanz-type bone screw rather than the yoke bone screw of the '909 Patent.

Thus, the screw described in the '263 Patent includes an elongated smooth shank portion. The connection assembly also adds a second washer disposed between the original washer and the smooth shank of the bone screw. The interdigitating feature exists between the contacting faces of the adjacent washers. The variable height is accomplished by a groove provided in the opposite surface of the additional washer that allows the connection assembly to slide along the shank of the bone screw until it is finally clamped together by a set screw.

While the connection assembly shown in the '263 Patent goes a step further toward an easy-to-implant variable angle, variable height assembly, it too has left some room for improvement. For example, the connector assembly of the '263 Patent requires an additional washer that adds to the number of components that must be manipulated by the surgeon. In addition, the added washer increases the lateral profile of the implant assembly. In certain regions of the spine, such as the thoracic and cervical regions, there is limited space transverse to the vertebral bodies. An optimal spinal implant system that has universal applicability should have as small a lateral profile as possible.

SUMMARY OF THE INVENTION

In order to address the unresolved detriments of prior implant systems, the present invention contemplates a variable angle/variable height connection assembly for a spinal implant system. In one embodiment of the invention, a connection assembly includes a first member or body that defines an opening through which an elongated spinal implant, such as a spinal rod, can extend. A second member is provided that includes a second opening through which extends an elongated stem or shank of a bone fastener, such as a bone screw or hook. The two members are attached by a connecting means that allows the members to pivot relative to each other about a connection axis. This connecting means thus provides a mechanism for variable angular orientations of the bone fastener relative to the elongated spinal implant. The second opening in the second member adds the height adjustment capability.

In a further feature of the invention, an interface washer is disposed over both the first and the second member of the connection assembly. The interface washer includes a first face having a groove defined therein for engagement with the elongated spinal implant extending through the opening in the first member. The interface washer also includes an opposite second face that is directed toward the stem of the bone fastener. This second face of the interface washer includes an interface element defined thereon. The shank of the bone fastener also includes a complementary interface element facing the interface washer.

In one specific embodiment, the second face of the interface washer includes a radially splined surface about a central opening. The central opening provides means for the washer to be passed over and about the first and second members of the connection assembly. The interface element on the shank of the bone fastener in this embodiment includes a rib extending along the length of the fastener. The rib is configured to reside between the radial splines of the interface washer.

With these components, the bone fastener can be moved up and down through the opening of the second member. In addition, the second member can be rotated relative to the first member so that the connection assembly can accommodate various angular orientations of the bone fastener relative to the elongated spinal implant. In the preferred embodiment, the central opening of the interface washer is non-circular to mate with a complementary non-circular profile of the first member of the connection assembly. The second member is sized so that it can be freely rotated within the central opening of the interface washer.

When the first and second members of the connection assembly are properly oriented relative to each other and to the bone fastener, a set screw can be threaded into the first member. The set screw includes an engagement tip for contacting the spinal rod within the opening of the first member. As the set screw is driven further into the first member, the engagement tip urges the spinal rod toward the shank of the bone fastener. Continued tightening of the set screw increases the clamping force between the spinal rod, interface washer, stem of the bone fastener, and ultimately a contact end of the opening in the second member.

In one embodiment of the invention, the rib of the bone fastener projects externally from an essentially constant diameter stem. In a further embodiment, the stem of the bone fastener includes a truncated surface along at least a portion of its length so that the shank has a non-circular transverse cross section. The interface element, or rib, then projects from the truncated surface. In an alternative embodiment, one or both of the interface washer and shank of the bone fastener can include a raised pattern, such as a crosshatch, multi-faceted, or knurled pattern. In a further embodiment, one of the interface washer or shank of the bone fastener can include a raised pattern, while the other of the two components can have a surface configured to permit penetration of the raised pattern.

In an alternative embodiment of the invention, a connection assembly includes a one-piece body that defines one opening for receiving the elongated spinal implant and a second substantially perpendicularly oriented opening for receive the stem of the bone fastener. One or both of the openings are configured to permit variable orientations of the elongated spinal implant within the first opening or the stem of the bone fastener within the second opening. In one specific embodiment, one or both of the openings are defined by a pair of channels that widen from a central portion of the opening outward toward the outer surface of the body.

In a further alternative embodiment, the elongated spinal implant can carry an interface element for engagement with an interface element on the intermediate washer. The intermediate washer can include a groove on its opposite surface to engage a smooth stem of the bone fastener. In this embodiment, the bone fastener maintains a fixed orientation relative to the interface washer, just as the spinal implant has a fixed orientation in the embodiments identified above. The bone fastener still retains its height adjustment capability. The variable angle adjustment is manifested between the spinal implant, or rod, and the interface washer.

In yet another embodiment, the elongated spinal implant, or rod, is clamped within the first body of the connection assembly by way of a second washer and a nut. In this embodiment, the connection assembly includes a first member defining an aperture for receiving the spinal implant, and a second member pivotably connected to the first member and defining an aperture for receiving a bone fastener. An interface washer is disposed between the spinal implant and the bone fastener in a manner implemented in other embodiments described above. With this embodiment, the first member can include a threaded stem projecting outward in a direction opposite the interface washer. A second washer is threaded over the first body so the spinal implant, or rod, is sandwiched between the interface washer and the second washer. An internally threaded nut is threaded onto the threaded stem to clamp the connection assembly together.

It is one object of the present invention to provide a spinal implant system that includes bone fasteners capable of achieving variable angular and height/vertical orientations relative to an elongated member spanning between locations along the spine. A further object is to provide this variable angle/variable height capability with a minimum number of components that must be manipulated by the surgeon within the surgical site.

One benefit of the invention is that the variable angle/variable height components can be easily clamped together to insure a solid fixation of the instrumented portion of the spine. A further benefit is achieved by features of the invention that permit top-tightening of the components within the patient.

These and other objects and benefits of the invention will be made clear upon consideration of the following written description and accompanying figures.

DESCRIPTION OF THE PREFERRED EMBODIMENTS

Figure 1:
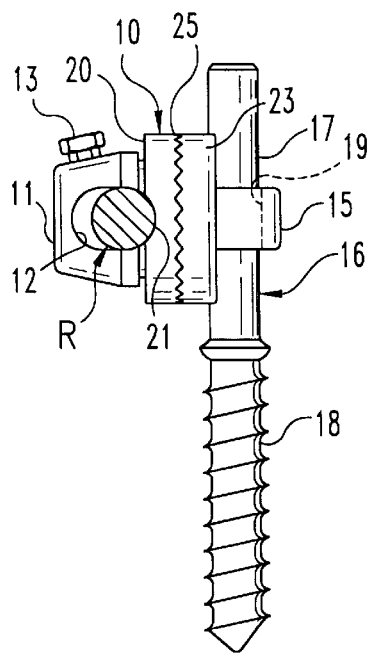
FIG. 1 is a side elevational view of a spinal implant connection assembly according to the prior system disclosed in U.S. Pat. No. 5,643,263.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention contemplates a variable angle and variable height connection assembly for connecting a bone fastener, such as a bone screw or hook, to an elongated spinal implant, such as a spinal rod, bar or plate. It is understood that the components of this connection assembly are formed of a medical grade material, preferably a metal such as stainless steel or titanium. It is also understood that the components are sized for introduction and implantation within the spine of a human patient. It is contemplated that the invention can be implanted at all levels of the spine, namely the cervical, thoracic, and lumbar levels, and from the posterior or anterior aspects of the spine. The components can be sized appropriately for each of the levels of the spine, with the overall size of the components being determinable by the ordinarily skilled artisan in the field of spinal implants.

Although the present invention has broad applicability, it is best understood with comparison to a prior art spinal implant connection assembly described in U.S. Pat. No. 5,643,263. In particular, the connection assembly 10 shown in FIG. 1 includes a rod connection member 11 that defines an elongated opening 12 through which a spinal rod R extends. A set screw 13 is threaded through the rod connection member 11, into the opening 12 and in contact with the spinal rod R.

Figure 2:
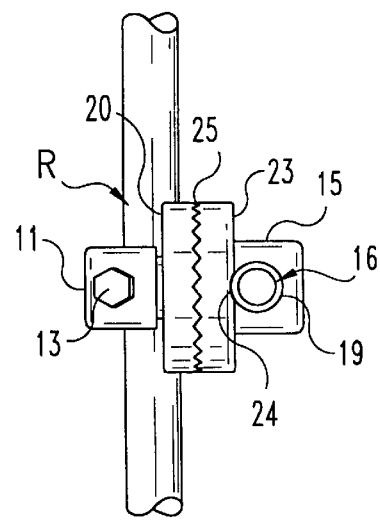
FIG. 2 is a top elevational view of the spinal implant assembly as shown in FIG. 1.

This prior art connection assembly 10 further includes a bolt connection member 15 defining a bolt opening 19 through which a bolt 16 extends. The bolt includes a non-threaded, smooth cylindrical post at one end and bone engaging threads 18 at an opposite end. The bolt connection member 15 is rotatably connected to the rod connection member 11 in a manner described in the '263 Patent with reference to FIGS. 1 and 2 of that patent, which description is incorporated herein by reference. Thus, the bolt connection member 15 is free to pivot or rotate relative to the rod connection member 11, which means that the bolt 16 can assume variable angular orientations relative to the rod R.

In order to fix this angular relationship, the connection assembly 10 includes a rod interface washer 20 and a bolt interface washer 23. The rod interface washer 20 includes an engagement groove 21, which receives the spinal rod R. Likewise the bolt interface washer 23 includes an engagement groove 24 into which is disposed the post 17 of the bolt 16. A spline interface 25 is provided between the two interface washers 20 and 23.

Figure 3:
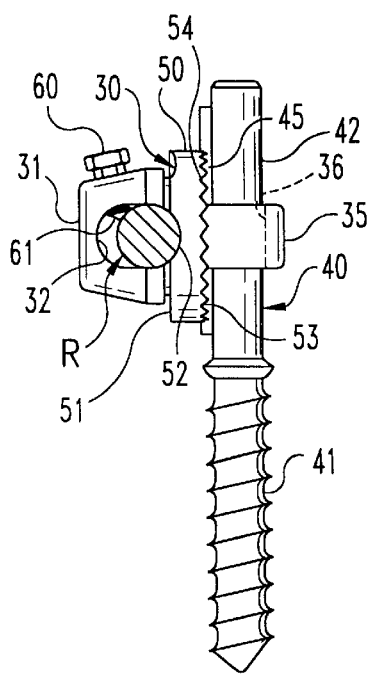
FIG. 3 is a side elevational view of a variable angle connection assembly according to one embodiment of the present invention.
Figure 4:
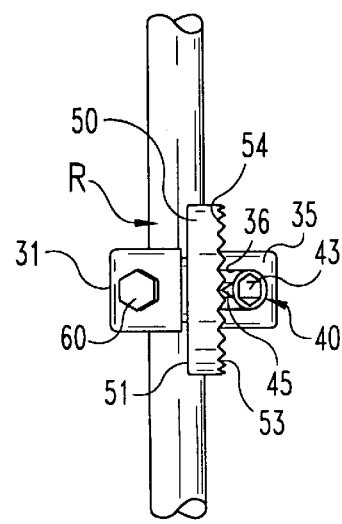
FIG. 4 is a top elevational view of the connection assembly as shown in FIG. 1.

Turning now to FIGS. 3–4, in accordance with the present invention, a connection assembly 30 is provided that permits similar variable angle and variable height adjustments to the position of the bone fastener relative to an elongated spinal implant. The elongated spinal implant can take a variety of forms, such as a rod or a plate. As a rod, the spinal implant can have a circular or a non-circular cross-section that is preferably configured to permit attachment of a connection assembly 30 at various positions along the length of the implant. Preferably, although not essentially, the spinal implant can also be configured to permit rotation of the connection assembly about the longitudinal axis of the implant.

In the illustrated embodiments, the bone fastener is a bone bolt or screw. It is understood that other bone fasteners are contemplated, such as various types of vertebral hooks and bone screws. In addition, the principles of the invention can be applied to other spinal implant components that are not necessarily engaged to a vertebra. For instance, variable angle and variable length positioning can be contemplated in connection with a transverse connector between two spinal implants running generally parallel to each other along a length of the spine. In addition, a laterally extending component can be attached to a spinal implant using the present inventive connection assembly, where other implants, such as bone fasteners, are attached to the laterally extending component.

In accordance with the preferred embodiment on the invention, the connection assembly 30 includes a first member 31 that defines a transverse opening 32 therethrough. The opening 32 is slightly elongated and is sized to receive an elongated spinal implant therethrough. More particularly the opening 32 is sized to slidingly receive a spinal rod R.

The connection assembly 30 also includes a second member 35 that a defines a second opening 36 therethrough. The opening 36 is sized to slidingly receive the stem of a bone fastener therethrough. The opening 36 is also elongated in a direction toward the first member 31.

Figure 9:
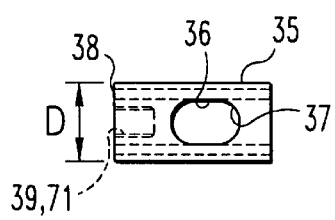
FIG. 9 is a top elevational view of a second member of the connection assembly shown in FIGS. 3 and 4.
Figure 10:
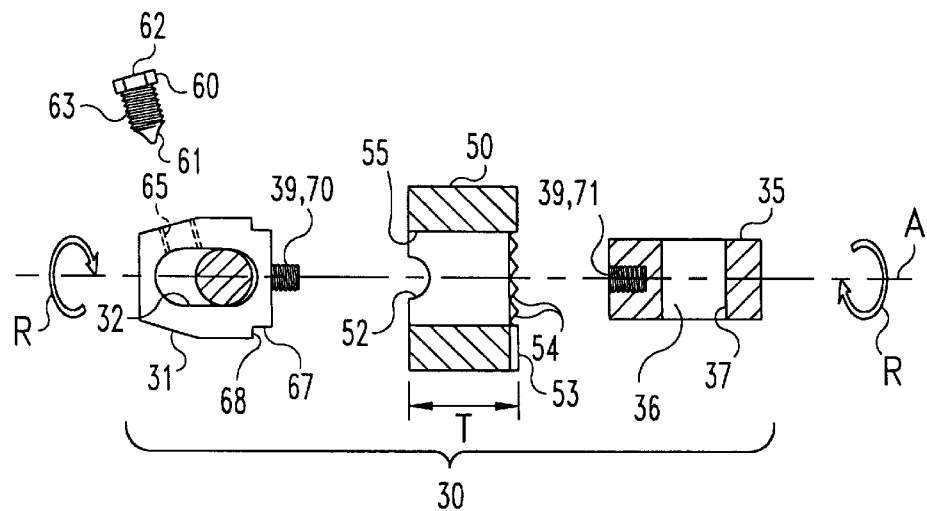
FIG. 10 is an exploded, partial cross section view, of the components of the connection assembly shown as FIGS. 3 and 4.

As shown best in the detail view of FIG. 9 and the exploded view of FIG. 10, the connection assembly 30 includes connecting means 39 between the first member 31 and the second member 35. This connecting means 39 is configured to permit relative pivoting between the two members about a connection axis A. More particularly, the two members can be individually rotated in the direction of the arrows R as shown in FIG. 10. The connecting means 39 can take a variety of forms. For instance, the connecting means 39 can constitute the snap-together swivel connection shown in FIGS. 1 and 2 of U.S. Pat. 5,643,263, and described at column 2, lines 31–46 of the patent which disclosure is incorporated here and by reference.

In the most preferred embodiment, the connecting means 39 includes a threaded post 70 extending from an end portion 67 of the first member 31. The connecting means 39 also includes a mating threaded bore 71 defined in the end face 38 of the second member 35. The relative rotation between the two components 31 and 35 can be achieved by threading or unthreading the post 70 relative to the bore 71. The pitch of the threads of the components means 39 can be controlled so that the separation between the first member 31 and second member 35 does not vary significantly even as the relative angular position between the two components changes. In addition, the threads on either or both of the post 70 and bore 71 can be configured in the nature of locking threads so the two components will maintain their angular positions prior to final clamping. As a further alternative, the length of the threads on either the post 70 or bore 71 can be limited since it is anticipated that only limited angular variations would be necessary in the use of the connection assembly 30. It is generally anticipated that angular variations of ±20–25° from the vertical would satisfy most spinal anatomies.

Figure 5:
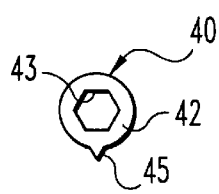
FIG. 5 is a top elevational view of a bone engaging fastener used with the connection assembly shown in FIGS. 3 and 4.
Figure 6:
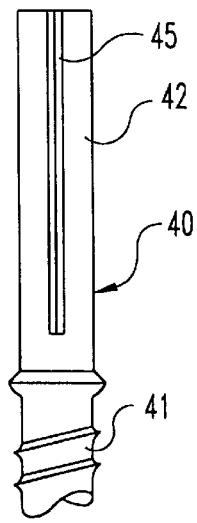
FIG. 6 is a side elevational view of the bone fastener shown in FIG. 5.

Referring back to FIGS. 3 and 4, as well as FIGS. 5 and 6, the bone fastener 40 includes a bone engaging portion 41 that is configured for attachment to a portion of the spine. In the illustrated embodiment, the bone engaging portion 41 constitutes bone engaging threads in the nature of a pedicle screw. As indicated above, other bone attachment configurations are contemplated by the invention.

The fastener 40 also includes an elongated stem 42 at the top portion of the fastener. An internal hex 43 (see FIGS. 4 and 5) is provided for engaging a tool for screwing the bone fastener 40 into a vertebrae. Alternatively, an external hex or driving portion can be provided for engagement by an appropriate driving tool. Where the bone fastener 40 is a spinal hook, the internal hex 43 is not essential, but gripping recesses may be added to the stem.

Figure 8:
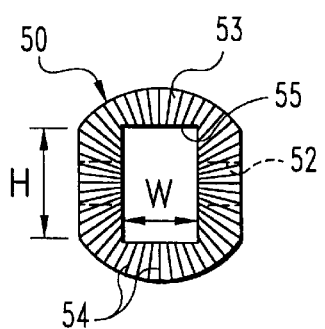
FIG. 8 is an end elevational view of an interface washer component of the connection assembly as shown in FIGS. 3 and 4.

In one aspect of the present invention, the bone fastener 40 includes an interface element 45 that is configured for interlocking engagement with the interface washer 50. Details of the interface washer 50 are shown in FIGS. 3, 4, and 8. The washer 50 includes a first face 51 that is orientated to the elongated spinal implant, or rod R. A rod groove 52 is formed in the first face 51. The rod groove is defined at a radius that is smaller than the radius of the spinal rod R. This design for the rod groove 52 is in accordance with the "3-point-shear clamp" feature of the TSRH® system. While the preferred embodiment of the present invention contemplates the use of a rod groove 52 for a circular rod R, other clamping or attachment mechanisms are contemplated. For example, the spinal rod R can be formed of a relatively softer material than the interface washer 50, while the first face 51 of the washer can include surface features configured to penetrate the rod R. Other rod clamping arrangements can be contemplated that can solidly fix the interface washer 50 to the rod R to prevent relative movement under spinal loads.

The interface washer 50 includes an opposite second face 53, shown most clearly in FIG. 8. This second face incorporates an interface element 54 that cooperates with the interface element 45 of the bone fastener 40. In accordance with one embodiment of the invention, the interface element 54 of the washer 50 includes a plurality of radially arranged splines. This spline configuration can be similar to the splined washer disclosed in U.S. Pat. No. 5,261,909, which can alternatively be described as alternating ridges or teeth. The radial pattern of the splines converge at the rotational center of the washer 50, or more particularly about the opening 55.

The interface element 45 of the bone fastener 40 in this embodiment constitutes a rib that is configured to reside between the splines of the interface element 54 on the second face 53 of the washer 50. The rib or interface element 45 of the bone fastener 40 preferably extends along substantially the entire length of the elongated stem 42. In this way, the height position of the stem 42 can be varied relative to the interface washer 50, while still retaining the interlocking relationship between the splines and the rib.

Figure 7:
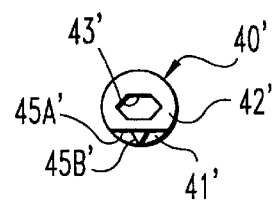
FIG. 7 is a top elevational view of an alternative embodiment of a bone fastener for use with the connection assembly shown in FIGS. 3 and 4.

In one embodiment of the bone fastener 40, the spline or interface element 45 projects from the outer diameter of the stem 42 as shown in FIG. 5. In an alternative embodiment, shown in FIG. 7, a bone fastener 40' includes a stem 42' that defines a truncated face 45A'. The interface element can then constitute a rib 45B' projecting from the truncated face. The bone fastener 40' can then be identical in all other aspects to the bone fastener 40 shown in FIGS. 5 and 6. The alternative bone fastener 40' shown in FIG. 7 requires different machining to fabricate than the bone fastener 40 shown in FIG. 5. One advantage of the alternative fastener 40' is that the truncated face 45A' shortens the lateral profile since the elongated stem 42' of the fastener 40' can be situated closer to the spinal rod R when the connection assembly is clamped together.

Figure 11:
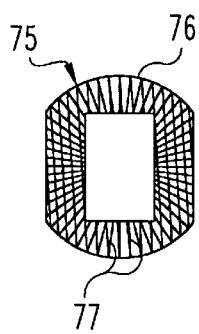
FIG. 11 is an end elevational view of an interface washer for use with a connection assembly in accordance with an alternative embodiment of the present invention.
Figure 12:
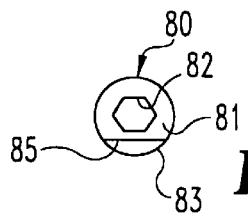
FIG. 12 is a top elevational view of a bone fastener for use with the interface washer shown in FIG. 11.
Figure 13:
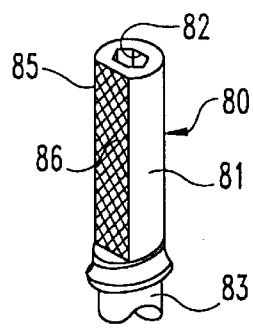
FIG. 13 is a side perspective view of the alternative embodiment of the bone fastener shown in FIG. 12.

Alternative interface connections between the bone fastener 40 and the washer 50 are also contemplated. For example, as shown in FIGS. 11–13, a variety of raised patterns can be formed on either or both the washer and the fastener. Thus, in a further alternative embodiment, an interface washer 75 can include a second face 76 having a raised pattern 77 defined thereon. The raised pattern can be in the nature of cross-hatching, multi-faceting, or knurling. Likewise, a bone fastener 80 as depicted in FIGS. 12 and 13, can include an elongated shank 81 with a truncated face 85. A raised pattern 86 can be defined on the truncated face 85 that provides for interdigitated engagement with the similarly configured interface washer 75. Like the bone fastener 40, the bone fastener 80 can include an internal driving hex 82 and a bone engaging portion 83.

In still another embodiment, one of either the bone fastener or the interface washer can be formed of a relatively softer material than the other. For instance, stem of the bone fastener, such as the fastener 80 in FIG. 13, can be formed of a relatively softer material than the interface washer, such as washers 50 (FIG. 8) or 75 (FIG. 11). The raised pattern on either interface washers can then penetrate the relatively softer material of the bone fastener stem to essentially interdigitate with the fastener.

With respect to the embodiment of the washer 75 shown in FIG. 11 and bone fastener 80 shown in FIGS. 12 and 13, the raised pattern must permit both the variable angle and variable height or vertical positioning of the components relative to each other. In a most preferred embodiment, a knurled pattern is applied to both components, which knurled pattern can constitute a large number of pyramid-shaped peaks and valleys.

To ensure fixation at variable angular positions, the washer 50 must remain stationary relative to the second member 35 and bone fastener 40. Referring to FIG. 8, the interface washer 50, includes an opening 55 that has a width W and a height H. Preferably the opening 55 is non-circular and conforms to the outer profile of the end portion 67 of the first member 31. With this configuration, the washer 50 can be slid onto the end portion 67 until it contacts a shoulder 68. The complementary non-circular profiles of the end portion 67 and opening 55 prevent rotation of the washer 50 relative to the first member 31. In this way, the washer can act as a rotational anchor for the bone fastener 40 when the connection assembly 30 is clamped together.

In order for the second member 35 to be permitted to rotate relative to the first member 31, the second member 35 is preferably cylindrical. The second member 35 can then have a diameter D that is less than the width W of the opening 55 in the interface washer 50. With this arrangement, the second member 35 can rotate relative to the first member even when the washer 50 is disposed about the first member and second member.

Returning again to FIGS. 3, 4, 9, and 10, the connection assembly 30 also includes a means for urging the elongated implant, or rod R, and the elongated stem 42 of the bone fastener 40 together. In a preferred embodiment, this means for urging includes a set screw 60 having an engagement tip 61 that is configured to contact the spinal rod R. The tip 61 can have a variety of shapes for translating the longitudinal motion of the set screw to a lateral force on the rod. The screw also includes a head 62 for engagement by a driving tool, and a series of screw threads 63 that are configured to be threaded into a complementary threaded bore 65.

The bore 65 is defined in the first member 31 and intersects the opening 32. The arrangement and alignment of the threaded bore 65 and set screw 60 is such that threading the screw into the bore exerts a lateral force on the spinal rod R pushing it toward one end of the opening 32. More specifically, as the set screw 60 is threaded into the bore 65, it gradually urges or pushes the spinal rod R toward the interface washer 50 and the second member 35. As depicted in the figures, the set screw is top-tightening; meaning that it is readily accessed directly posterior to the connection assembly. This feature reduces the lateral profile of the connection assembly and makes final tightening of the assembly much easier for the surgeon.

In the use of the connection assembly 30, the bone fastener 40 is engaged to a specific vertebra at a desired orientation. The rod R is manipulated so that the assembly 30, which has been pre-threaded on the rod is aligned with the stem 42 so the second member 35 can be dropped onto the fastener with the stem 42 projecting through the second opening 36. As the rod R is nestled into position along the spine, the second member 35 pivots relative to the first member 31 attached to the rod. As the rod is finally positioned, the second member 35 floats along the stem until the final height alignment is achieved.

As the set screw 60 is threaded into the bore 65, it pushes the rod into contact with the rod groove 52 of the interface washer 50. Continued tightening of the set screw urges the interface washer 50 against the stem 42 of the bone fastener 40. At this point, the connection assembly 30 has assumed its final height and angular orientation.

With the first member 31 and second member 35 in their proper angular relationship, and with the connection assembly 30 at its proper height relative to the bone fastener 40, further tightening of the set screw pushes the stem 42 of the fastener into the contact end 37 of the elongated opening 36. Thus, the final clamping is effected between engagement tip 61 of the set screw 60, and the contact end 37 of the opening 36 of the second number 35. Further tightening of the set screw 60 to a predetermined torque value insures a firm connection between the rod R and the rod groove 52, and between the interface element 45 of the bone fastener 40 and element 54 of the interface washer 50. A torque limiting set screw 60 can be provided in which the head 62 of the screw shears off at a predetermined torque so that over-tightening of the set screw is avoided.

In a further aspect of the connection assembly 30, the interface washer 50 has a thickness T that is calibrated to permit solid tightening of the connection assembly 30 about the rod R and bone fastener 40. The interface washer 50 is disposed simultaneously over both the first member and the second member. Thus, the washer can maintain contact with the spinal rod R before it is urged to the end of the opening 32. In addition the washer can maintain contact with the stem 42 of the bone fastener 40 when the stem is pressed into the contact end 37 of the elongated opening 36.

Figure 14:
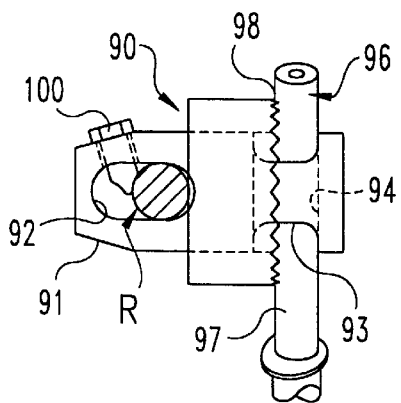
FIG. 14 is a side elevational view of a variable angle/variable height connection assembly according to another embodiment of the present invention.
Figure 15:
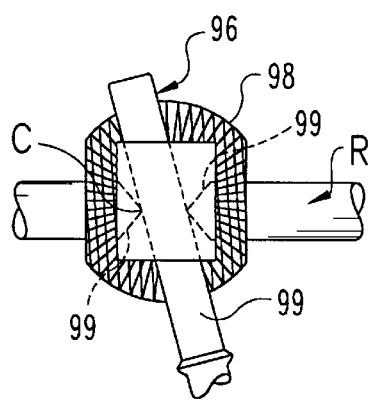
FIG. 15 is an end elevational view of the connection assembly shown in FIG. 14.

A further alternative embodiment of the invention is depicted in FIGS. 14 and 15. In this embodiment, a connection assembly 90 is provided that includes a one-piece body 91. The body defines an elongated rod opening 92 and an elongated bolt opening 93. The axes through the two openings are mutually perpendicular, while the openings are both elongated in the same direction. The bolt opening 93 defines a contact end 94 at one end of the body 91 against which the bolt 96 is pressed when the connection assembly 90 is finally tightened. The connection assembly 90 also includes an interface washer 95, which can be similar to any of the interface washers described above. The washer 95 is threaded over the body 91 between the rod R and the bolt 96, and more particularly the stem 97 of the bolt. The interface washer 95 and bolt 96 can include interface engagement means, which means 98 can include any of the interface elements described above.

With this embodiment, the bolt opening 93 is configured to permit angular variation of the position of the stem 97 relative to the rod R. Thus, in one embodiment, the bolt opening 93 is defined by a pair of diverging or widening channels 99 that open at the top and bottom of the body 91. In the illustrated embodiment, the channels converge at a center portion C located generally at the mid point of the body 91. The bolt opening 93 has a width at the center position sufficient to receive the stem 97 of the bolt 96 therethrough. The center position C of the opening 93 essentially acts as a fulcrum about which the body 91 can be pivoted relative to the bolt 96 to properly orient the body. With this embodiment, the widening channels 99 diverge at a predetermined angle based upon the anticipated range of angular orientation of the bolt 96 relative to the connection assembly 90.

Figure 16:
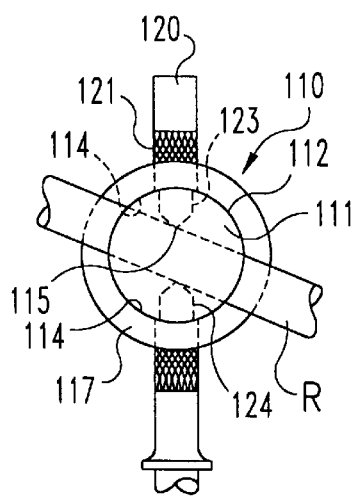
FIG. 16 is an end elevational view of a variable angle and height connection assembly according to a further embodiment of the invention.
Figure 17:
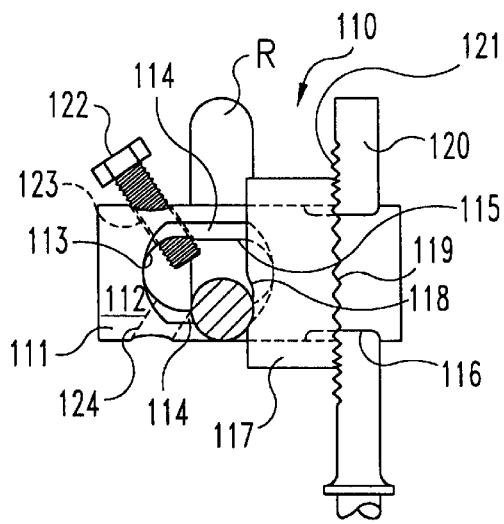
FIG. 17 is a side elevational view of the connection assembly depicted in FIG. 16 with a fixation set screw added.

In an alternative embodiment, depicted in FIGS. 16 and 17, the widening channel approach is utilized at the interface between the connection assembly and the elongated spinal implant. In this embodiment, a connection assembly 110 includes a one-piece body 111 that has a generally cylindrical outer surface or profile 112. The body defines an elongated first aperture 113 configured to receive an elongated spinal implant, such as rod R, therein. The body also defines an elongated second aperture oriented substantially perpendicular to the first aperture and configured to receive the stem of a bone fastener 120 therethrough.

As with the embodiment of FIGS. 14 and 15, the connection assembly 110 includes an interface washer 117 defining a groove 118 for receiving the spinal implant. The opposite face of the washer includes an interface element 119 for complementary engagement with an interface element 121 on the bone fastener 120. In this embodiment, the interface washer 119 can define a circular opening for passage over the cylindrical surface 112 of the body 111. Thus, the washer 117 is free to rotate about the body 111. The orientation of the washer will be fixed when the assembly 110 is tightened because the spinal implant R will engage the washer at the groove 118.

In contrast to the prior embodiment, the first aperture 113 includes opposite diverging channels 114. The channels converge at a center point 115 within the body 111, with the gap at the being sufficient to receive the spinal implant R therethrough. As depicted in the FIGS. 16 and 17, the implant R can assume variable angular orientations relative to the connection assembly 110, and particularly the body 111. In this embodiment, the second aperture 116 for the bone fastener 120 can have a uniform cross-section, or can also include the diverging channels, as shown in FIG. 15. It is understood that the diverging channel features (channels 99 of FIG. 15, and/or channels 114 of FIG. 16) can be implemented in the earlier described embodiments of the invention to provide additional angular degrees of freedom for the inventive connection assembly.

In the prior embodiments it has been assumed that the elongated spinal implant, such as the rod R, is engaged within a groove of the interface washer, such as groove 52 of washer 51 (FIGS. 3 and 10) or groove 118 of washer 117 (FIG. 17). In another embodiment, the connection assembly can include the sub-assembly components 130 shown in FIG. 18. With this embodiment, the elongated spinal implant 131. includes an interface element 132. An interface washer 134 can include a mating interface element 135 directed toward the implant 131. The interface elements 132, 135 can be of any of the forms described above provided they are sufficient to fix the washer and implant from relative rotation or movement.

The opposite face of the washer 134 can define a groove 136 to receive the stem 139 of a bone fastener 138. Preferably, the stem 139 is a smooth stem, although it may include various surface features to enhance fixation with the washer 134.

Figure 18:
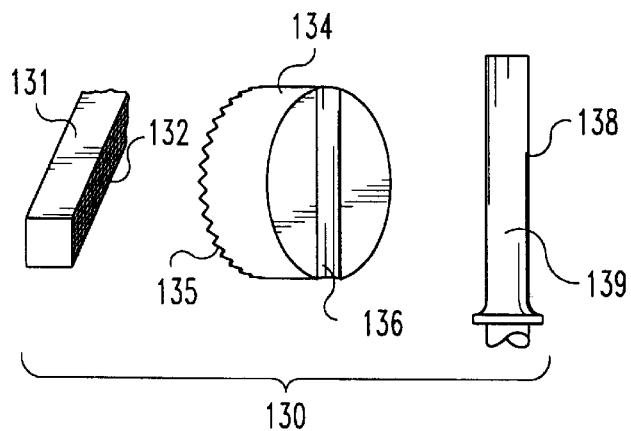
FIG. 18 is an exploded perspective view of components of a connection sub-assembly according to yet another embodiment of the present invention.

With this embodiment of FIG. 18, the variable angle capability is accomplished between the elongated implant 131 and the washer 134. Although the bone fastener 138 has a fixed angular orientation relative to the washer, it can achieve variable height orientations. In the illustrated embodiment, the spinal implant 131 is depicted as an elongated bar having a substantially flat surface defining the interface element 132. The implant 131 can have a circular cross-section, with the interface element being defined around the entire surface of the implant. As a further alternative, the spinal implant 131 can be formed of a relatively softer material than the washer 134. In this alternative approach, the interface element 135 of the washer 134 can be configured to penetrate the implant 131, thereby locking the two components against relative movement.

Figure 19:
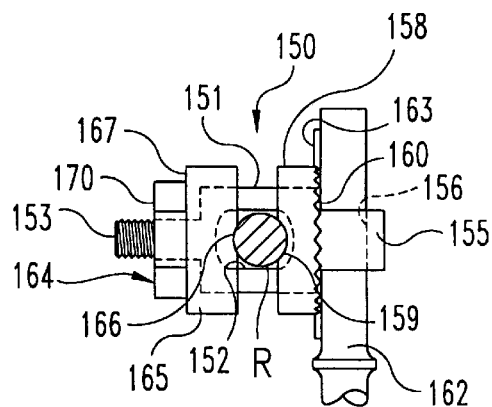
FIG. 19 is a side elevational view of a variable angle/height connection assembly in accordance with still a further embodiment of the invention.

Referring now to FIG. 19, a connection assembly 150 is illustrated that can be similar to the assembly 50 shown in FIG. 3–10. This, the assembly 150 can include a first member 151 defining an elongated aperture 152 for receiving a spinal implant R therethrough. The assembly also includes a second member 155 that is rotatably connected to the first member in a manner described above. The second member also defines an aperture 156 for receiving a bone fastener 162 therethrough.

As with the prior embodiment, the connection assembly 150 also includes an interface washer 158 that defines a groove 159 for receiving the implant R and an opposite interface element 160 for mating with an interface element 163 of the bone fastener 162.

Thus far, the connection assembly 150 is configured and operates like the assembly 50 described above. However, unlike the prior assembly, the assembly 150 does not utilize a set screw threaded through one of the members. Instead, a means for urging 164 is provided that includes a clamping washer 165 that contact the spinal implant. The clamping washer 165 preferably defines a groove 166 for receiving the spinal implant R, although the groove is not necessary for the clamping the assembly together.

The first member 151 defines a threaded post 153 projecting outward and away from the interface washer 158. The clamping washer 165 is threaded over the post 153 and first member 151 so that the spinal implant R is sandwiched between the interface washer 163 and clamping washer 165. A nut 170 can be threaded onto the threaded post 153 to contact the clamping washer 165 and urge it into the implant R. As the nut is tightened further, the stack including the clamping washer 165, implant R, interface washer 158 and bone fastener 162 are clamped together.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

For example, the first member 31 as described must be pre-loaded onto the rod. However, the member can be configured for top-loading onto the rod by incorporating the top-loading features of the connector depicted in FIG. 4 of U.S. Pat. No. 5,562,662 as described at column 7, lines 10–13, and as depicted in FIGS. 3A–3C and described at column 5, line 56—column 8, line 11, which descriptions are incorporated herein by reference.

In addition, in the illustrated embodiment the means for urging, or set screw 60, is engaged within the first member 31. Alternatively, the clamping force can be applied at the second member 35. In this instance, the tip of the set screw would preferably be modified from the configuration shown in FIG. 10 of the present application. This alternative arrangement for the means for urging can be configured like the connector shown in FIGS. 3A–3C of the '662 Patent and described at column 5, line 6—column 8, line 11, which description has been incorporated by reference. With this alternative approach, the set screw would act against the stem 42 of the bone fastener 40 to push the stem against the washer 50, which then urges the rod R against the opposite end of the opening 32. A similar alternative configuration can be implemented with the clamping assembly 164 illustrated in FIG. 19.

The bone fastener 40 has been described as including a generally circular cross-section stem 42. Non-circular cross-sections can be utilized provided hat the shape accommodates solidly clamping the stem 42 within the opening 36 in the second member. The contact end 37 of the opening 36 can have a complementary shape. As a further alternative, either or both the contact end 37 and stem 42 can have a surface roughening or interdigitating feature to enhance the clamping effect and resistance against slipping.

The washer 50 is described as including a groove 52 for clamping the rod R. Other clamping features are contemplated that provide a solid fixation to the rod. In addition, the clamping feature can be modified to accommodate variations in the shape of the elongated spinal implant. For instance, the rod R can have a non-circular cross section.

In one of the illustrated embodiments, the two members 31 and 35 are connected by a connecting means 39 that permits relative rotation between the two components. Alternatively, the connecting means can provide for variable lateral separation between the two members, either alone or with the relative rotation capability. Thus, where the connecting means 39 includes the threaded post 70 and bore 71, the thread pitch can be modified to permit coarse adjustments in the lateral separation as one member is rotated relative to the other. Where the connecting means is limited to providing lateral separation adjustments, the second opening 36 in the second member 35 can be configured like the opening 93 in the embodiment of the one-piece body 91.

In yet another alternative embodiment, the interface element 45 on the bone fastener 40 can have varying degrees of prominence. In the illustrated embodiment, the interface element or rib 45 projects 0.04–0.10 inches from the stem 41. The rib can project farther from the stem, with a commensurate decrease in the thickness T of the interface washer 50.

What is claimed is:

1. A spinal implant assembly engageable to an elongated spinal implant configured to span a length of the spine, comprising:
   a bone fastener having an elongated stem at one end and an opposite end configured to engage a bone of the spine, said elongated stem having an engagement surface;
   a first member defining a first opening sized to slidingly receive the elongated spinal implant therethrough;
   a second member defining a second opening to slidingly receive said elongated stem of said bone fastener therethrough;
   means for connecting said first member to said second member for rotation about a connection axis substantially perpendicular to an axis of said first opening and an axis of said second opening;
   one washer defining an opening for positioning said washer over said first member and said second member and between said first opening and said second opening, said one washer having a first face contacting a portion of the elongated spinal implant when the implant extends through said first opening, and an opposite second face adjacent said engagement surface of said bone fastener when the stem extends through said second opening; engagement means between said second face and said engagement surface of said elongated stem for resisting rotation of said bone fastener relative to said washer; and means for urging the elongated spinal implant and the elongated stem of the bone fastener together to clamp about said one washer.

2. The spinal implant assembly according to claim 1, wherein said engagement means includes:
   a plurality of splines defined at said second face of said washer and radially emanating from said opening; and
   at least one rib defined at said engagement surface of said elongated stem of said bone fastener, said at least one rib configured to engage said second face of said washer between adjacent ones of said plurality of splines.

3. The spinal implant assembly according to claim 1, wherein said engagement means includes:
   a first raised pattern defined at said second face of said; and
   a second raised pattern defined at said engagement surface of said elongated stem of said bone fastener,
   wherein said first and said second raised patterns are configured for complementary engagement to prevent relative movement between said washer and said bone fastener.

4. The spinal implant assembly according to claim 3, wherein at least one of said first and second raised patterns constitutes knurling.

5. The spinal implant assembly according to claim 1, wherein said engagement means includes:
   a raised pattern defined at one of said second face of said washer or said engagement surface of said bone fastener; and
   the other of said second face and said engagement surface being formed of a relatively softer material than said one of said second face of said washer or said engagement surface,
   wherein said raised pattern is configured to penetrate said relatively softer material when said bone to prevent relative movement between said washer and said bone fastener.

6. The spinal implant assembly according to claim 5, wherein said raised pattern constitutes knurling.

7. The spinal implant assembly according to claim 1, wherein:
   said first opening is elongated from a first end to a second end adjacent said second member along an axis that is substantially parallel to said connection axis; and
   said means for urging includes a bore intersecting said first opening at said first end and an urging member extendable through said bore to urge the elongated spinal implant within said first opening toward said second end of said first opening.

8. The spinal implant assembly according to claim 7, wherein:
   said bore is threaded; and
   said urging member is a set screw having a tip configured to contact the elongated spinal implant within said first opening.

9. The spinal implant assembly according to claim 7, wherein said second opening is elongated along an axis that is substantially parallel to said connection axis, whereby the elongated stem of the bone fastener can slide along said second opening from a first end adjacent said first member and an opposite second end.

10. The spinal implant assembly according to claim 9, wherein said one washer has a thickness sufficient so that said washer urges the elongated stem of the bone fastener against said second end of said second opening in response to the elongated spinal implant being urged into said washer by said urging member.

11. The connection assembly according to claim 1, wherein said means for urging includes:
   a threaded stem projecting from said one of said first member and said second member;
   a clamping washer defining an opening therethrough for mounting said clamping washer over said threaded stem and said one of said first member and said second member, said clamping washer having a surface for contacting a corresponding one of the spinal implant and the bone fastener extending through said one of said first member and said second member; and
   a nut threadedly engaged on said threaded stem.

12. The spinal implant assembly according to claim 1, wherein said first face of said one washer includes a groove arranged to engage the elongated spinal implant when the implant is within said first opening.

13. The connection assembly according to claim 1, wherein at least one of said first opening and second opening has a width that increases from a location within said opening to the surface of a corresponding one of said first member or said second member.

14. The spinal implant assembly according to claim 1, wherein:
   said first member defines a non-circular profile; and
   said opening of said one washer is complementary with said non-circular profile.

* * * * *